United States Patent
Chen et al.

(12) 
(10) Patent No.: US 6,362,382 B1
(45) Date of Patent: Mar. 26, 2002

(54) UNCATALYZED FLUORINATION OF 240FA

(75) Inventors: Bin Chen, Treddyfrin; Michael S. Bolmer, Lower Providence, both of PA (US)

(73) Assignee: Atofina Chemicals, Inc., Phila., PA (US)

( * ) Notice: Subject to any disclaimer, the term of this patent is extended or adjusted under 35 U.S.C. 154(b) by 0 days.

(21) Appl. No.: 09/910,375

(22) Filed: Jul. 20, 2001

(51) Int. Cl.⁷ ................................................ C07C 17/08
(52) U.S. Cl. ........................................................ 570/164
(58) Field of Search .......................................... 570/164

(56) References Cited

FOREIGN PATENT DOCUMENTS

| JP | 10101593 | 4/1998 |
| JP | 11180908 | 7/1999 |

*Primary Examiner*—Alan Siegel
(74) *Attorney, Agent, or Firm*—William D. Mitchell; Stanley A. Marcus

(57) ABSTRACT

An uncatalyzed process is provided for the fluorination of 240 fa in the presence of a solvent.

1 Claim, No Drawings

UNCATALYZED FLUORINATION OF 240FA

BACKGROUND OF THE INVENTION

This invention relates to the uncatalyzed fluorination of 1,1,1,3,3-pentachloropropane ("240 fa") in the presence of a solvent to produce fluorinated products selected from one or more of $CCl_aF_{3-a}CH\!=\!CHCl$ and $CCl_bF_{3-b}CH_2CHCl_cF_{2-c}$ where a, b and c are each equal to 0, 1 or 2. The fluorinated product 245 fa (where b and c equal 0) is useful as a foam blowing agent and refrigerant. The other fluorinated products are intermediates for 245 fa.

Previous attempts to fluorinate 240 fa without the use of catalysts, as disclosed in Japanese Patent Applications 10101593 and 11180908, have resulted in a low level of fluorination, while catalyzed fluorination of 240 fa, such as with antimony pentachloride, increases corrosivity of the reactants and selectivity to undesired oligomer formation.

BRIEF SUMMARY OF THE INVENTION

An uncatalyzed process for the fluorination of 240 fa is provided, which process comprises (a) contacting 240 fa with hydrogen fluoride ("HF") in the presence of tetramethylene sulfone under conditions sufficient to produce fluorinated products selected from one or more of $CCl_aF_{3-a}CH\!=\!CHCl$ and $CCl_bF_{3-b}CH_2CHCl_cF_{2-c}$ where a, b and c are separately selected from 0, 1 or 2; and (b) separating the fluorinated products from the resulting reaction mixture in (a).

DETAILED DESCRIPTION

It has now been found that use of tetramethylene sulfone as a solvent in the uncatalyzed fluorination of 240 fa reduces the formation of heavy by-products and increases the reaction rate and the extent of fluorination. The extent of fluorination (E) is determined by dividing the number of fluorines added to a molecule by the number of chlorine and double bonds on the reactant.

The process of this invention can be conducted as a batch or semi-continuous process. The HF:240 fa molar ratio is typically from 10 to 200, preferably from 20 to 100. The tetramethylene sulfone:240 fa molar ratio is typically from 0.5 to 20, preferably from 1 to 5. The temperature is typically from 30 to 200° C., preferably from 75 to 125° C. The pressure is typically from about 0 to 500 psig, preferably from 120 to 250 psig. Residence time is typically from about 5 minutes to 8 hours, preferably from about 0.5 to 3 hours. The by-product HCl can be removed from the resultant reaction mixture by methods known in the art such as by absorption (in water or caustic) or by distillation. The HCl can also be continuously removed from the reactor during the reaction by distillation. The practice of the invention is illustrated in more detail in the following non-limiting example.

EXAMPLE 14.4 g of 240 fa, 116 g of HF and 8.4 g of tetramethylene sulfone were placed in an autoclave (HF/240 fa=90:1). The contents were heated to 100° C. for 3 hours. The pressure reached 280 psig. Conversion was 100%. Selectivity was 7.8% for 241 fa (b and c=2), 0.7% for 242 fa (b=1 and c=2), 0.4% for 1232 zd (a=1), 0.2% (b=0 and c=2), 69.5% for 1233 zd (a=0), 1.9% for 244 fa (b=0 and c=245 fa (b and c=0), and 1.4% for others. E=0.63. By comparison, when the solvent was omitted, E was only 0.37, conversion was 83%, and selectivity was only 2.5% for fluorinated products other than 241 fa and 1233 zd.

We claim:

1. An uncatalyzed process for the fluorination of 1,1,1,3,3-pentachloropropane which comprises (a) contacting 1,1,1,3,3-pentachloropropane with hydrogen fluoride in the presence of tetramethylene sulfone under conditions sufficient to produce fluorinated products selected from one or more of $CCl_aF_{3-a}CH\!=\!CHCl$ and $CCl_bF_{3-b}CH_2CHCl_cF_{2-c}$ where a, b and c are separately selected from 0, 1 or 2; and (b) separating the fluorinated products from the resulting reaction mixture in (a).

* * * * *